United States Patent
Kramer et al.

(10) Patent No.: US 6,268,523 B1
(45) Date of Patent: Jul. 31, 2001

(54) PROCESS FOR THE PREPARATION OF A TERTIARY PERESTER

(75) Inventors: Gerardus F. H. Kramer, Wageningen; Folkert P. Cuperus, Staphorst; Johannes T. P. Derksen, Cuyck; John Meijer, Deventer; Marinus C. Tammer, Schalkhaar, all of (NL)

(73) Assignee: Akzo Nobel NV (NL)

( * ) Notice: Subject to any disclaimer, the term of this patent is extended or adjusted under 35 U.S.C. 154(b) by 0 days.

(21) Appl. No.: 09/490,309

(22) Filed: Jan. 24, 2000

Related U.S. Application Data

(63) Continuation of application No. PCT/EP98/04181, filed on Jul. 3, 1998.

(30) Foreign Application Priority Data

Jul. 25, 1997 (EP) ................................................. 97202353

(51) Int. Cl.⁷ .................................................. C07C 69/00
(52) U.S. Cl. ........................... 560/302; 435/197; 435/198
(58) Field of Search .......................... 560/302; 435/197, 435/198

(56) References Cited

U.S. PATENT DOCUMENTS 4,798,793    1/1989    Eigtved ................................ 435/134

FOREIGN PATENT DOCUMENTS

| 322213 | 6/1989 | (EP) | C12P/7/64 |
|---|---|---|---|
| 424130 | 4/1991 | (EP) | C12N/11/00 |
| WO 91/04333 | * 4/1991 | (WO) | . |
| 94/01541 | 1/1994 | (WO) | C12N/9/20 |
| 91/04333 | 4/1999 | (WO) | C12P/7/40 |

OTHER PUBLICATIONS

N. Baba et al., "Enzymatic Resolution of Racemic Hydroperoxides in Organic solvent", Agric. Biol. Chem., 52(10), 2685–2687 (1988).*
Derwent Abstract No. 80–54684C (1980).
European Patent Publication No. 140,542 (1985)—abstract only.
European Patent Publication No. 238,023 (1987)—abstract only.
Chemical Abstracts, vol. 113, 210919j (1990).
Chemical Abstracts, vol. 114, 228093r (1991).
E. Höft et al., "Enzyme–Catalyzed Kinetic Resolution of Racemic Secondary Hydroperoxides", Tetrahedron:Asymmetry, vol. 5, No. 2, pp. 603–608 (1995).
N. Baba et al., "Lipase–Catalyzed Kinetic Resolution of Racemic Methyl 13–Hydroperoxy–9Z,11E–Octadecadienoate in an Organic Solvent", Agric. Biol. Chem., 54 (12), 3349–3350 (1990).

* cited by examiner

*Primary Examiner*—Ralph Gitomer
*Assistant Examiner*—Devesh Khare
(74) *Attorney, Agent, or Firm*—Richard P. Fennelly

(57) ABSTRACT

The invention relates to a process for the preparation of a tertiary perester by contacting an acyl compound with a tertiary hydroperoxide in the presence of an enzyme catalyst. The acyl compound has the formula $R^1[C(O)OR^2]_n$, wherein $R^1$ is a linear or branched, saturated or unsaturated $C_1$–$C_{22}$ group, optionally containing one or more hetero atoms, $R^2$ represents hydrogen or has the same meaning as described for $R^1$, and n is 1–5, or a polyalcohol ester of $R^1C(O)OH$, wherein $R^1$ has the same meaning as described above. The tertiary hydroperoxide has the formula $[HOOCR^3R^3]_mR^4$, wherein $R^3$ represents either a methyl or an ethyl group, $R^4$ has the same meaning as described for $R^1$, and m is 1–5.

12 Claims, No Drawings

PROCESS FOR THE PREPARATION OF A TERTIARY PERESTER

This application is a continuation of PCT/EP98/04181 filed Jul. 3, 1998.

BACKGROUND OF THE INVENTION

This invention relates to a process for the preparation of a tertiary perester by contacting an acyl compound with a tertiary hydroperoxide.

Tertiary peresters are commercially important initiators for the polymerization of monomers in particular, to acrylics, polyethylene, polyvinylchloride, and styrenics. Tertiary peresters are also used for the modification of these and other polymers. For the various methods of synthesis of peresters we refer to D. Swern, Ed., *Organic Peroxides*, Volumes I and II, 1970 and 1971, respectively, Wiley-Interscience, New York. On a commercial scale, tertiary peresters are prepared from tertiary hydroperoxides and acid chlorides in particular. This process has the disadvantage that acid chlorides are expensive starting materials. A further drawback is that the use of acid chlorides leads to the formation of hydrogen chloride, which is a corrosive. Also, the use of acid chlorides presents a problem in the form of chloride waste. Accordingly, there is a need for improved methods of preparing tertiary peresters.

Incidentally, Baba et al., *Agric. Biol. Chem.* 52 (1988) 2685–2687 describe the occurrence of enzymatic synthesis of hydroperoxides in the course of an enzymatic resolution of racemic secondary hydroperoxides in organic solvent by reaction with isopropenyl acetate in the presence of a lipoprotein lipase from Pseudomonas fluorescens (LPL Amano P). In this way, one enantiomer is acylated while the other enantiomer remains in the reaction mixture as the hydroperoxide. Acylated primary and secondary hydroperoxides are said to disintegrate spontaneously to carboxylic acid and aldehyde or ketone, respectively. More importantly, it is mentioned that no acylation reaction occurred starting from 1-methyl-1-phenylpropyl hydroperoxide.

Höft et al. in *Tetrahedron: Asymmetry* 5 (1995) 603–608 also describe that 1-methyl-1-phenylpropyl hydroperoxide and 1-cyclohexyl-1-phenylethyl hydro-peroxide are not converted into the corresponding tertiary peresters using the same lipase.

Further, several publications describe the enzyme-catalyzed synthesis of peracids. In PCT Patent Publication No. WO 91/04333, for example, a process for preparing peroxycarboxylic acids from a carboxylic acid and hydrogen peroxide using an enzyme catalyst is described. The preparation of tertiary peresters is not disclosed in these publications.

SUMMARY OF THE INVENTION

Surprisingly, we have found a new, commercially attractive process to prepare tertiary peresters which does not suffer from the above-mentioned disadvantages. The process according to the present invention is characterized in that an acyl compound of formula $R^1[C(O)OR^2]_n$, wherein $R^1$ is a linear or branched, saturated or unsaturated $C_1$–$C_{22}$ group, optionally containing one or more hetero atoms, $R^2$ represents hydrogen or has the same meaning as described for $R^1$, and n is 1–5, or a polyalcohol ester of $R^1C(O)OH$, wherein $R^1$ has the same meaning as described above, is contacted with a tertiary hydroperoxide of formula $[HOOCR^3R^3]_mR^4$, wherein $R^3$ represents either a methyl or an ethyl group, $R^4$ has the same meaning as described for $R^1$, and m is 1–5, in the presence of an enzyme catalyst.

DESCRIPTION OF PREFERRED EMBODIMENTS

The term "tertiary peresters" in the present application refers to peresters in which the peroxy α-carbon atom is a tertiary carbon atom.

Typically, in accordance with the formulae previously described, $R^1$ is a $C_1$–$C_{22}$ alkyl, $C_3$–$C_{22}$ cycloalkyl, $C_6$–$C_{22}$ aryl, $C_7$–$C_{22}$ aralkyl, or $C_7$–$C_{22}$ alkaryl group. Preferably, $R^1$ is a linear or branched $C_1$–$C_{11}$ alkyl group or a phenyl group, $R^2$ is hydrogen or a methyl or ethyl group, n is 1 or 2, $R^3$ is a methyl group, m is 1 or 2, and/or $R^4$ is a linear or branched $C_1$–$C_5$ alkyl group or a phenyl group. More preferably, $R^4$ is a methyl, ethyl, propyl, neopentyl, or phenyl group, most preferably a methyl or ethyl group. Most preferably, n and m are 1. It is preferred that when $R^3$ is an ethyl group, $R^4$ is a linear or branched $C_1$–$C_5$ alkyl group. Polyalcohol esters of $R^1C(O)OH$ can also be used in the invention process and are attractive acyl compounds. A particularly preferred class of polyalcohol esters are glycerol esters, so-called glycerides. Either one, two, or all three hydroxy groups of glycerol may be esterified with $R^1C(O)OH$. Triglycerides are most preferred since they are readily available. Glycerol esters can be isolated from natural sources, e.g. animals and plants fats and oils, and they typically contain fatty acyl groups having 12 to 22 carbon atoms, namely, $R^1$ is a $C_{12}$–$C_{22}$ group. These fatty acyl groups may be saturated or unsaturated, and may contain functional groups such as hydroxy groups, as for example in ricinoleic acid.

Typical examples of tertiary hydroperoxides which can be used in the invention process include: tert-butyl hydroperoxide, 1,1-dimethyl-1-propyl- (or tert-amyl) hydroperoxide, 1,1-dimethyl-1-butyl- (or tert-hexyl) hydroperoxide, 1-methyl-1-ethyl-1-propyl-hydroperoxide, 1,1,2-trimethylpropyl-1-hydro-peroxide, cumyl hydroperoxide, 1,1-dimethyl-3-hydroxy-1-butyl- (or hexylene-glycol) hydroperoxide, 1,1,3,3-tetramethylbutyl-hydroperoxide, 2,5-dimethyl-2,5-dihydroperoxyhexane, 2,5-dimethyl-2,5-dihydroperoxyhex-3-yn, cyclo-hexane-1, 4-di-(2-propyl-2-hydroperoxide), cyclohexane-1,3-di-(2-propyl-2-hydroperoxide), benzene-1,4-di-(2-propyl-2-hydroperoxide), and benzene-1,3-di-(2-propyl-2-hydroperoxide).

Typical examples of acyl compounds which can be used in the process according to the invention include: acetic acid, phenylacetic acid, phenoxyacetic acid, propanoic acid, isobutyric acid, benzoic acid, 2-methyl-benzoic acid, 2-methylbutanoic acid, 2-butenoic acid, 3-phenylpropenic acid, 2,2-dimethylpropanoic acid, 2,2-dimethylbutanoic acid, 2,2-dimethyl-pentanoic acid, 2-ethylhexanoic acid, 3,5,5-trimethylhexanoic acid, 2-ethylbutanoic acid, neohexanoic acid, neoheptanoic acid, neodecanoic acid, octanoic acid, nonanoic acid, lauric acid, 2,4,4-trimethylpentanedioic acid, hexanedioic acid, 2,2,4-trimethylhexanedioic acid, 2,4, 4-trimethylhexanedioic acid, decanedioic acid, undecanedioic acid, dodecanedioic acid, cyclo-hexanecarboxylic acid, 1,4-cyclohexanedicarboxylic acid, cyclohexane-1,4-diacetic acid, maleic acid, citric acid, 3-hydroxybutanoic acid, 4-hydroxybutanoic acid, 2-hydroxy-pentanoic acid, 3-hydroxypentanoic acid, 4-hydroxypentanoic acid, 5-hydroxypentanoic acid, hydroxyacetic acid, 2-hydroxyisobutyric acid, 2-hydroxypropanoic acid, 2-hydroxyhexanoic acid, hydroxypivalic acid, hydroxy-succinic acid, methylsuccinic acid, citraconic acid, fumaric acid, oxalic acid, terephthalic acid, propenoic acid, phthalic acid, 3-ketopentanoic acid, 4-ketopentanoic acid, and 3-ketoglutaric acid, and their corresponding methyl esters, ethyl esters, n-propyl esters, isopropyl esters, n-butyl esters, sec-butyl esters, isobutyl esters, ethylene glycol esters, and propylene glycol esters.

Specific examples of tertiary peresters which can be prepared by the process according to the present invention include:
cumyl peroxyneodecanoate
2,4,4-trimethylpentyl-2 peroxyneodecanoate
tert-amyl peroxyneodecanoate
tert-butyl peroxyneodecanoate
tert-amyl peroxypivalate
tert-butyl peroxypivalate
2,5-bis(2-ethylhexanoylperoxy)-2,5-dimethylhexane
tert-amyl peroxy-2-ethylhexanoate
tert-butyl peroxy-2-ethylhexanoate
tert-butyl peroxydiethylacetate
tert-butyl peroxyisobutanoate
tert-butyl peroxy-3,5,5-trimethylhexanoate
tert-butyl peroxyacetate
tert-butyl peroxybenzoate
1,4-bis(tert-butylperoxycarbo)cyclohexane Two compounds having two tertiary perester functionalities are 2,5-bis(2-ethylhexanoylperoxy)-2,5-dimethylhexane and 1,4-bis(tert-butyl-peroxy-carbo)-cyclohexane. The first compound is prepared by reacting a bistertiary hydroperoxide, i.e., m=2, and an acyl compound, the second is synthesized by contacting a cyclohexane-derived bisacyl compound, i.e., n=2, with a tertiary hydroperoxide.

$R^1$ and $R^4$ may optionally contain one or more heteroatoms. One or more heteroatoms may form functional groups. Typical examples of functional groups that may form part of the substituents $R^1$ and/or $R^4$ include ether, hydroxy, ketone, acid, ester, amine, and amide groups, and halogen atoms. Hydroxy and ester groups are preferred.

The enzyme catalyst employed in the process according to the invention preferably is a hydrolytic enzyme. Suitable examples include esterases, proteases and lipases of microbial, plant, or mammalian origin. Hydrolytic enzymes of mammalian origin may be obtained from, for instance, rat, horse, or pig. Hydrolytic enzymes from plants may be obtained, for example, from papaya, wheat germ, or oats. Lipases are particularly preferred catalysts.

The suitability of a given enzyme for use in the invention process is easily tested by exposing a tertiary hydroperoxide to an acyl compound, for example, a carboxylic acid, carboxylic ester or fatty acyl glycerol ester, in the presence of the enzyme (preferably with removal of reaction water in case when a carboxylic acid is used) and monitoring the formation of tertiary perester from the reaction as illustrated by the procedures described in the examples below.

The enzyme may be used as such, but it may also be chemically modified or immobilized in order to enhance its stability and its activity towards the substrates in question and/or to facilitate the recovery of the enzyme catalyst after the reaction.

Typical examples of esterases that can be employed in the process according to the invention include those from horse liver, pig liver, and from microbial strains of Acinetobacter, Amycolatopsis (e.g. orientalis), Arthrobacter, Saccharomyces (e.g. cerevisiae), Candida (e.g. rugosa, lipolytica), Escherichia (e.g. coli (*Penicillin acylase*)), Mucor (e.g. miehei), Nocardia, and Streptomyces (e.g. bambergiensis).

Typical examples of proteases include Trypsin and the ones isolated from microbial strains of Aspergillus (e.g. sojae, niger, saitoi), Bacillus (e.g. licheniformis), Penicillium, Rhizopus, Serratia, Staphylococcus (e.g. aureus), and Streptomyces (e.g. caespitosus).

Lipases which may be employed in the present process include porcine pancreatic lipase or microbial lipases produced by strains of Acinetobacter, Aeromonas, Agrobacterium, Arthrobacter, Bacillus (e.g. subtilis), Beauveria, Botrytis, Brevibacterium, Candida (e.g. antarctica), Chaetomium, Chromobacterium (e.g. viscosum), Cladosporium, Eucherichia, Lactobacillus, Micrococcus, Mycobacterium, Nocardia, Penicillium (e.g. simplicissimum), Pseudomonas (e.g. aeroginosa, pseudoalcaligenes, cepacia, fluorescens, glumae, putida, mendocina, fragi), Rhizomucor (e.g. miehei), Rhizopus (e.g. delemar, oryzae), Rhodotorula (e.g. rubra), Staphylococcus (e.g. hyicus, epidermis), Streptococcus, Streptomyces, and Trichoderma.

Preferred lipases for use according to the process of the invention are those produced by species of Bacillus, Candida, Rhizomucor, Pseudomonas, and Rhizopus. Lipases from Candida antarctica and Rhizomucor miehei are particularly preferred.

It is known to produce and modify hydrolytic enzymes by recombinant DNA techniques, see for instance PCT Patent Publication No. WO 94/01541 and European Patent Publication No. 238,023. Recombinant hydrolytic enzymes may also be employed for the present purpose.

When employed in the process according to the invention, the enzyme catalyst may be in a soluble state, for instance, a precipitate obtained from the fermentation fluid or a spray-dried or freeze-dried preparation. However, in order to facilitate the separation of product and catalyst after the reaction, it is preferred to immobilize the enzyme.

Immobilization procedures are well known in the art and are described, for instance, in "Immobilized Enzymes", K. Mosbach, Ed., *Methods in Enzymology*, Volume 44, 1976, Academic Press, New York. These procedures include covalent coupling to insoluble organic or inorganic supports, or within enzyme crystals, i.e., so-called cross-linked enzyme crystals, entrapment in (polymeric) gels, and adsorption to ion-exchange resins or other organic or inorganic materials.

Suitable support materials for immobilization of enzymes include silicas, silicates, e.g., glass; chitin; chitosan; silicon polymers, e.g., siloxanes; cationic or anionic ion-exchange resins; organic polymers, e.g., polyacrylamides, polyethylenes, polypropylenes, polyvinyl chlorides, polysulfones, polyether sulfones, polyurethanes, polystyrenes, polyvinyl acetates, polymethyl methacrylates, latex, nylon, teflon, dacron, polyvinyl alcohols, or any copolymers of monomers forming these polymers; and polysaccharides, e.g., dextran or agarose.

A preferred support material is macroporous polypropylene, for instance, ACCUREL EP100 of Akzo Nobel. The enzyme catalyst may be adsorbed on this material, for example, according to the procedures disclosed in European Patent Publication Nos. 322,213 or 424,130. Other preferred support materials are polystyrene-, acrylic-, or phenol-formaldehyde-based ion-exchange resins. Immobilization of enzyme catalysts on such types of resin is disclosed, for instance, in U.S. Pat. No. 4,798,793 and European Patent Publication No. 140,542.

The process of the invention is conveniently carried out by contacting a tertiary hydroperoxide with a carboxylic acid or carboxylic ester in the presence of an enzyme catalyst in a suitable reaction vessel for a sufficient amount of time. During the reaction $R^2OH$, water in the case of a carboxylic acid is being used or glycerol in the case a triglyceride is being used, is formed. Suitable reaction vessels include round-bottomed flasks, packed or solid bed columns/reactors, fluidized bed columns/reactors, and batch columns/reactors equipped with membrane or distillation systems.

Typically, the reaction time in the small-scale test reactions of the examples varies from several hours to several days. In these cases the conversion rates range from 8% after six hours in Example 24 to more than 95% after seven hours in Example 17.

The invention process can be carried out in a wide range of molar ratios of tertiary hydroperoxides to acyl compounds having an excess either of tertiary hydroperoxide or carboxylic acid/carboxylic ester/polyalcohol ester. Typically, the molar ratio of tertiary hydroperoxide to acyl compound varies between 0.05 and 20. A preferred molar ratio range is from 0.1 to 10. It is more preferred to use about equimolar amounts of tertiary hydroperoxide and acyl compound. In another embodiment of the invention process the tertiary hydroperoxide is used as a solvent.

The amount of enzyme catalyst to be added is dependent on several factors that are known to the person skilled in the art of enzyme reactions and these include the reactivity of the tertiary hydroperoxide and acyl compound, the reaction conditions such as temperature and reaction time, the type of reactor, and whether the enzyme catalyst is immobilized or not. For the small-scale reaction vessel used in the examples that illustrate the invention process it typically varies between 0.1 and 400 weight percent, based on the weight of tertiary hydroperoxide added.

The process of the present invention can be carried out with or without the addition of an organic solvent. It is preferred to use a solvent if a carboxylic acid is used as the acyl compound in order to remove the reaction water formed during the process. Suitable organic solvents include alcohols, such as isopropyl alcohol and tertiary butanol; hydrocarbons, such as pentane, hexane, cyclohexane, and heptane; chlorinated hydrocarbons, aromatic solvents such as toluene, and ethers such as diethyl ether. Hydrocarbons are preferred solvents in the process according to the invention.

When a carboxylic ester is employed as the acyl compound, in particular when a low boiling ester is used, an excess of the ester can be used. In this case, the carboxylic ester also serves as a solvent in the reaction.

The process according to the invention can be performed within a wide temperature range. The reaction temperature is determined by the denaturation temperature of the enzyme catalyst and/or the decomposition temperature of the tertiary perester that is being formed during the process. Typically, it is carried out at elevated temperature in the range of 20–100° C.

The invention process typically is performed at atmospheric pressure. When less temperature stable tertiary peresters are being produced it may be convenient to carry out the reaction at a lower pressure. In such a case, the reaction may also be carried out at temperatures of below 20° C.

If the reaction is carried out in a vessel instead of in a column, it is preferred to stir the reaction mixture.

In the course of the formation of the tertiary perester from a tertiary hydroperoxide and a carboxylic acid reaction water is formed. This reaction water preferably is removed from the reaction mixture, for example by way of azeotropic distillation, using a suitable solvent, molecular distillation, pervaporation, stripping with (dried) air or an inert gas, such as nitrogen, or by the addition of molecular sieves, preferably 3 Å or 4 Å molecular sieves. It is more preferred to azeotropically distill off the reaction water or to strip with dried air.

When in the invention process the tertiary perester is prepared from a tertiary hydroperoxide and a carboxylic ester, it is preferred to distill off the alcohol, i.e., $R^2OH$, formed during the reaction.

The products obtained by the process according to the 3invention are used for the polymerization of monomers, for example, to acrylics, polyethylene, polyvinyl chloride, and styrenics. These products are also useful for the modification of these polymers and others.

The invention is illustrated by the following Examples.

EXAMPLES

Hydroperoxides:
Tert-butyl hydroperoxide, 70% in water, from Arco (the hydroperoxide in pentane or isooctane after water separation and drying is used).
Tert-amyl hydroperoxide, 85% in water, from Akzo Nobel
1,1,3,3-Tetramethylbutyl hydroperoxide, 91%, from Akzo Nobel Cumyl hydroperoxide, 80%, from Huls
1,1-Dimethylbutyl hydroperoxide, 93%, from Kayaku Akzo Corporation Enzymes:
Candida antarctica lipase B immobilised on acrylate, NOVOZYM SP 435, from Novo Nordisk
Rhizomucor miehei, LIPOZYME IM20, from Novo Nordisk, immobilised on a resin
Pseudomonas pseudoalcaligenes, from Genencor, immobilised on CELITE or polypropylene (ACCUREL brand from Akzo Nobel)
Pseudomonas cepacia, from Amano Pharmaceutical, AMANO PS-C and AH-S immobilised on ceramic material/celite Acyl compounds:
Isobutyric acid, p.a., from Merck
Caprylic acid, 98%, from Fluka
Heptanoic acid, 98%, from Acros
Hexanoic acid, 98%, from Acros
Polyunsaturated, partly conjugated, octadecanoic acid, NOURACID HE 456, from Akzo Nobel
Ricinoleic acid, Nouracid CS 80, from Akzo Nobel
Pivalic acid, from Acros
3,5,5 trimethylhexanoic acid, from Huls
2-ethylhexanoic acid, from Acros
Hexanedioic acid, from Janssen Chimica
6-Bromohexanoic acid, from Acros
2-Bromohexanoic acid, from, Acros
5-Phenylpentanoic acid, from Acros
4-Oxopentanoic acid, from Janssen Chimica
Methyl acetate, p.a., from Merck
Castor oil (triglyceride with 85–90% ricinoleic acid), from Akzo Nobel Others:
Molecular sieves 3 Å, from Baker
Tert-butyl methyl ether, from Janssen Chimica
Isooctane (2,4,4-trimethylpentane), from Baker The formation of the tertiary peresters was monitored by means of thin-layer chromatography, capillary gas chromatography (GC) (Chrompack CP Sil 5 CB MS column, hydrogen carrier gas, FID detection), and/or by way of Fourier transform infrared (FT-IR) spectroscopy.

All tertiary peresters that are prepared in the examples described below were isolated and analyzed by standard techniques as illustrated in Example 20.

Example 1

Equimolar amounts of tert-butyl hydroperoxide (31 mmoles; 3 M in toluene) and caprylic acid (octanoic acid, 31 mmoles) were dissolved in 50 ml of pentane in a round-bottomed flask with stirring, and 800 mg of NOVOZYM 435 enzyme were added. The reaction mixture was stirred and heated to reflux temperature. The reaction water was removed by azeotropic distillation. The distillate was cooled, the pentane was separated and reintroduced into the reaction vessel. After seven hours of reaction GC analysis showed that more than 90% of the substrates was converted into tert-butylperoxy caprylate.

Example 2

To tert-butyl hydroperoxide (31 mmoles; 3 M in toluene) and 10 molar equivalents of methyl acetate were added 800 mg of NOVOZYM 435 enzyme. The reaction mixture was heated to 45° C. and, after twenty-four hours of reaction, GC analysis showed 30% conversion (TLC analysis showed that more than 80% of the hydroperoxide was converted into tert-butylperoxy acetate).

Example 3

Tert-butyl hydroperoxide (31 mmoles; 3 M in toluene) and isobutyric acid (31 mmoles) were dissolved in 50 ml of pentane and 800 mg of NOVOZYM 435 enzyme were added. Reaction water was removed by azeotropic distillation. After thirty hours of reaction, GC analysis showed more than 80% conversion of the substrates into tert-butylperoxy isobutyrate.

Examples 4–6

Following the procedure described in Example 1, tert-butylperoxy hexanoate (in Example 4), tert-butylperoxy heptanoate (in Example 5), and tert-amylperoxy octanoate (in Example 6) were prepared from tert-butyl hydroperoxide and hexanoic acid, tert-butyl hydroperoxide and heptanoic acid, and tert-amyl hydroperoxide and octanoic acid, respectively. The conversions as measured by FT-IR were in all cases greater than 70%.

Example 7

To a reaction vial with a TEFLON fluoropolymer magnetic stirring rod, 3 ml containing 0.2 M tert-butyl hydroperoxide, and 0.2 M 2-ethylhexanoic acid in isooctane was added. The reaction was started by addition of 200 mg of Rhizomucor miehei enzyme and about 25 mg of molsieves (7 grains). After sixty-seven hours, 15% conversion to tert-butyl peroxy-2-ethylhexanoate was obtained as measured with GC.

Example 8

Following the procedure of Example 7, but with Candida antarctica as the enzyme catalyst, 11% conversion to tert-butyl peroxy-2-ethylhexanoate was obtained after twenty-four and one half hours of reaction time.

Example 9

To a reaction vial with a TEFLON fluoropolymer magnetic stirring rod, 3 ml containing 0.2 M tert-butyl hydroperoxide and 0.2 M pivalic acid in isooctane was added. The reaction was started by addition of 200 mg of Rhizomucor miehei enzyme and about 10 mg of molsieves (3 grains). After sixty-seven hours, 13% conversion to tert-butyl peroxypivalate was obtained as measured with GC.

Examples 10–12

Following the procedure of Example 9 but using other enzymes the following results were obtained:

| Example | Enzyme | Reaction time | Conversion |
|---|---|---|---|
| 10 | Pseudomonas pseudoalcaligenes (on ACCUREL) | 48 hrs | 10% |
| 11 | Pseudomonas cepacia PS-C | 67 hrs | 17% |
| 12 | Pseudomonas cepacia AH-S | 67 hrs | 33% |

Example 13

To a reaction vial with a TEFLON fluoropolymer magnetic stirring rod, 3 ml containing 0.2 M tert-butyl hydroperoxide and 0.2 M 3,5,5-trimethylhexanoic acid in isooctane was added. The reaction was started by addition of 200 mg of Candida antartica enzyme and about 10 mg of molsieves (3 grains). After twenty-fourand one-half hours, 11.2% conversion to tert-butyl peroxy-3,5,5-trimethylhexanoate was obtained as measured with GC.

Example 14

To a reaction vial with a TEFLON fluoropolymer magnetic stirring rod, 3 ml containing 0.2 M tert-butyl hydroperoxide and 0.2 M 5-phenylpentanoic acid in isooctane was added. The reaction was started by addition of 200 mg of NOVOZYM 435 enzyme and about 25 mg of molsieves (7 grains). After two and one half hours, 32% conversion to tert-butyl peroxy-5-phenylpentanoate was obtained as measured with FT-IR Examples 15 and 16

Following the procedure of Example 14 but using other acids the following results were obtained:

| Example | Acid | Reaction time | Conversion |
|---|---|---|---|
| 15 | 2-bromohexanoic acid | 47 hrs | 35% |
| 16 | 4-oxopentanoic acid* | 16 hrs | 22% |

*using tert-butylmethylether as the solvent

Example 17

Tert-butyl hydroperoxide (93 mmoles) and hexanedioic acid (15.5 mmoles) were dissolved in 50 ml of pentane in a round-bottomed flask with stirring, and 800 mg of NOVOZYM 435 enzyme were added. The reaction mixture was stirred at 35° C. The reaction water was removed by azeotropic distillation. The distillate was cooled, the pentane the separated and reintroduced into the reaction vessel. After seven hours of reaction, more than 95% of conversion to 1,4-bis-(tert-butylperoxycarbo)butane was obtained as measured with FT-IR.

Example 18

Tert-butyl hydroperoxide (160 mmoles) and ricinoleic acid (120 mmoles) were dissolved in 375 ml of pentane in a round-bottomed flask with stirring, and 1 g of NOVOZYM 435 enzyme was added. The reaction mixture was stirred at 35° C. The reaction water was removed by azeotropic distillation. The distillate was cooled, the pentane was separated and reintroduced into the reaction vessel. After twenty-seven hours of reaction, 93% conversion to tert-butylperoxyricinolate was obtained as measured with FT-IR.

Example 19

Following the procedure of Example 18, but with NOU-RACID HE456 being used, a conversion of 99% after thirty hours of reaction was obtained.

Example 20

Tert-butyl hydroperoxide (31 mmoles) and octanoic acid (31 mmoles) were dissolved in 50 ml of pentane in a round-bottomed flask with stirring, and 800 mg of NOVOZYM 435 enzyme were added. The reaction mixture was stirred at 35° C. The reaction water was removed by azeotropic distillation. The distillate was cooled, the pentane was separated and reintroduced into the reaction vessel. After five hours of reaction, more than 80% conversion to tert-butyl peroxy-octanoate was obtained as measured with FT-IR.

The reaction was stopped, the reaction mixture was cooled to 20° C. and filtered over a G-3 glass filter. The filtrate was washed three times with a diluted aqueous sodium hydroxide solution (pH 13) to remove unreacted tertiary hydroperoxide and octanoic acid and was washed subsequently with a n aqueous sodium bicarbonate solution (pH 8). The pentane was removed in vacuo at room temperature giving the perester in 80% yield having a content of 98.3%. FT-IR analysis shows a carbonyl peak at 1774 cm$^{-1}$.

Examples 21–24

Following the procedure of Example 20 but using other tert-hydroperoxides the following results were obtained:

| Example | Tert-hydroperoxide | Reaction time | Conversion |
|---|---|---|---|
| 21 | tert-amyl hydroperoxide | 4 hrs | 40% |
| 22 | 1,1-dimethylbutyl hydroperoxide | 7 hrs | 52% |
| 23 | 1,1,3,3-tetramethylbutyl hydroperoxide | 6 hrs | 28% |
| 24 | Cumyl hydroperoxide | 6 hrs | 8% |

Example 25

Tert-butyl hydroperoxide (160 mmoles) and castor oil (120 mmoles) were dissolved in 375 ml of pentane in a round-bottomed flask with stirring, and 1 g of NOVOZYM 435 enzyme was added. The reaction mixture was stirred at 35° C. for twenty-eight hours. FT-IR analysis showed a 40% conversion to tert-butyl peroxyricinolate.

What is claimed is:

1. A process for the preparation of a tertiary perester by contacting an acyl compound with a tertiary hydroperoxide in the presence of an enzyme catalyst, wherein the acyl compound is of the formula $R^1[C(O)OR^2]_n$, wherein $R^1$ is a linear or branched, saturated or unsaturated $C_1$–$C_{22}$ group, optionally containing one or more hetero atoms, $R^2$ represents hydrogen or has the same meaning as described for $R^1$, and n is 1–5, or a polyalcohol ester of $R^1C(O)OH$, wherein $R^1$ has the same meaning as described above, and the tertiary hydroperoxide is of formula $[HOOCR^3R^3]_mR^4$, wherein $R^3$ represents either a methyl or an ethyl group, $R^4$ has the same meaning as described for $R^1$, and m is 1–5.

2. A process according to claim 1 wherein the enzyme is a hydrolase.

3. A process according to claim 2 wherein the hydrolase is a lipase.

4. A process according to claim 3 wherein the lipase is obtained from *Candida antarctica*.

5. A process according to claim 1 wherein the enzyme is an immobilized enzyme.

6. A process according to claim 1 wherein the reaction is carried out in an organic solvent.

7. A process according to claim 1 wherein $R^2OH$, which is formed during the reaction, is removed from the reaction mixture.

8. A process according to claim 1 wherein $R^3$ is a methyl group.

9. A process according to claim 1 wherein $R^4$ is a methyl, ethyl, propyl, neopentyl, or phenyl group.

10. A process according to claim 1 wherein $R^1$ is a linear or branched $C_1$–$C_{11}$ alkyl group or a phenyl group.

11. A process according to claim 1 wherein n or m is 1 or 2.

12. A process according to claim 1 wherein the acyl compound is a glycerol triester of $R^1C(O)OH$.

* * * * *